United States Patent [19]

Long, Jr.

[11] Patent Number: 5,847,009
[45] Date of Patent: Dec. 8, 1998

[54] PROPHYLAXIS IN THE PARENTERAL ADMINISTRATION OF PARTICULATE DISPERSIONS IN FLUOROCARBON EMULSIONS

[75] Inventor: David M. Long, Jr., El Cajon, Calif.

[73] Assignee: Alliance Pharmaceutical Corp., San Diego, Calif.

[21] Appl. No.: 138,485

[22] Filed: Oct. 15, 1993

Related U.S. Application Data

[63] Continuation-in-part of Ser. No. 417,796, Oct. 4, 1989, Pat. No. 5,284,645, which is a continuation-in-part of Ser. No. 82,846, Aug. 5, 1987, Pat. No. 4,987,154, which is a continuation-in-part of Ser. No. 818,690, Jan. 14, 1986, Pat. No. 4,865,836.

[51] Int. Cl.$^6$ .......................... A61K 31/02; A61K 31/03; A61K 31/58; A61K 33/14

[52] U.S. Cl. .......................... 514/743; 424/673; 514/748; 514/937; 514/174; 514/182; 514/177

[58] Field of Search .................... 424/10, 673; 514/743, 514/748, 937, 177, 174, 182

[56] References Cited

U.S. PATENT DOCUMENTS

| | | | |
|---|---|---|---|
| 3,975,512 | 8/1976 | Long, Jr. | 424/5 |
| 4,073,879 | 2/1978 | Long, Jr. | 424/5 |
| 4,278,654 | 7/1981 | Rakli et al. | 424/5 |
| 4,285,928 | 8/1981 | Wada et al. | 424/5 |
| 4,415,556 | 11/1983 | Bretschneider | 424/5 |
| 4,865,836 | 9/1989 | Long, Jr. | 424/5 |
| 4,927,623 | 5/1990 | Long, Jr. | 424/5 |
| 4,951,673 | 8/1990 | Long | 128/653 |
| 4,987,154 | 1/1991 | Long, Jr. | 424/5 |
| 5,670,495 | 9/1997 | Goodin et al. | 514/178 |

FOREIGN PATENT DOCUMENTS

| | | |
|---|---|---|
| 517547 | 5/1981 | Australia . |
| 0220153 | 3/1986 | European Pat. Off. . |
| 0307087 | 12/1989 | European Pat. Off. . |
| 8900848 | 2/1989 | WIPO . |

OTHER PUBLICATIONS

Abe, H., et al. (1985) Role of histidine–related compounds to intracellular buffering in fish skeletal muscle. Am. J. Physiol. 249:R449–R454.

Aiken, J., et al. (1981) Endogenous prostacyclin contributes to the efficacy of a thromboxane synthetase inhibitor for preventing coronary artery thrombosis. Jour. of Pharmacology and Experimental Therapeutics 219(2):299–308.

Cadnapaphornchai, P., et al. (1982) Effect of imidazole on the recovery from bilateral ureteral obstruction in dogs. Amer. J. Physio. 243:F532–F536.

Cao, Y.–Z., et al. (19870 Regulation by vitamin E of phosphatidylcholine metabolism in rat heart. Biochem. J. 247:135–140.

Ferrari, F. and Baggio, G. (1985) Influence of imidazole on behavioral effects induced by dopaminergic agonists in rats. Life Sciences 36:1397–1405.

Ferrari, F., et al. (1986) Imidazole has similar behavioural effects to yohimbine. Psychopharmacology 88:58–62.

Ferrari, F., et al. (1987) Effects of imidazole and some imidazole–derivatives on lisuride–induced mounting and aggressiveness. Psychopharmacology 93:19–24.

Ferrari, F., et al. (1985) Behavioural pharmacology of imidazole, a potential antidepressant agent. Arch. Int. Pharmacodyn 277:303–312.

Fitzgerald, G.A., et al. (1983) Endogenous prostacyclin biosynthesis and platelet function during selective inhibition of thromboxane synthase in man. J. Clin. Invest. 71:1336–1343.

Golino, P., et al. (1989) Simultaneous administration of thromboxane $A_2$—and serotonin $S_2$—receptor antagonists markedly enhances thrombolysis and prevents or delays reocclusion after tissue–type plasminogen activator in a canine model of coronary thrombosis. Circulation 79:911–919.

Guo, et al. Liposomes in Drug Delivery: 21 years on the school of pharmacy, University of London, 12th–15th Dec. 1990.

Kazic, T. (1977) Action of methylxanthines and imidazole on the contractility of the terminal ileum of the guinea pig. European J. of Pharmacology 41:103–111.

Kresh, J., et al. (1987) The relative buffering power of cardioplegic solutions. J. of Thoracic and Cardiovascular Surgery 93(2):309–311.

Lianos, E.A., et al. (1983) Glomerular prostaglandin and thromboxane synthesis in rat nephrotoxic serum nephritis. J. Clin. Invest. 72:1439–1448.

Maguire, E. and Wallis, R. (1983) In vivo redirection of prostaglandin endoperoxides into 6–keto $PGF_{1\alpha}$ formation by thromboxane synthetase inhibitors in the rat. Thrombosis Research 32:15–27.

Matheson, I., et al. (1975) The quenching of singlet oxygen by amino acids and proteins. Photochemistry and Photobiology 21:165–171.

Miller, D. et al. (1984) CT of the liver and spleen with EOE–13: review of 225 examinations. Am. Jour. of Rad. 143:235–243.

Needleman, P., et al. (1977) Thromboxane synthetase inhibitors as pharmacological tools: differential biochemical and biological effects on platelet suspensions. Prostaglandins 14(5):897–907.

Needleman, P., et al. (1979) Platelet and blood vessel arachidonate metabolism and interactions. J. Clin. Invest. 63:345–349.

(List continued on next page.)

*Primary Examiner*—Theodore J. Criares
*Attorney, Agent, or Firm*—Knobbe,Martens, Olson & Bear LLP

[57] ABSTRACT

Methods for preventing or ameliorating the transient adverse physiological response to particulate dispersions (TAPR response) when these dispersions are administered parenterally to a patient. The methods comprise the administration of a prophylactic anti-inflammatory drug prior to administration of the particulate-containing material, and optionally during administration as well. Preferred drugs are cyclooxygenase inhibitors and corticosteroids.

25 Claims, 8 Drawing Sheets

OTHER PUBLICATIONS

Needleman, P., et al. (1977) Application of imidazole as a selective inhibitor of thromboxane synthetase in human platelets. Proc. Natl. Acad. Sci. 74(4):1716–1720.

Nilsson, K. et al. (1976) Contraction of glycerol extracted fibres of smooth muscle by acetylcholine and imidazole in the presence of a Ca–binding microsomal fraction from rabbit colon. Acta Physiol. Scand. 98:407–411.

Ogletree, M., et al. (1985) Pharmacological actions of SQ 29,548, a novel selective thromboxane antagonist. J. of Pharmacol. and Exper. Therapeutics 234(2):435–441.

Okegawa, T., et al. (1983) Endotoxin induces chronic prostaglandin and thromboxane synthesis from ureter–obstructed kidneys: role of inflammatory cells. J. of Pharmacology and Experimental Therapeutics 225(1):213–218.

Parkhouse, W., et al. (1985) Buffering capacity of deproteinized human vastus lateralis muscle. J. Appl. Physiol. 58(1):14–17.

Patterson, G., et al. (1985) Effects of imidazole and indomethacin on fluid balance in isolated sheep lungs. J. Applied Physiol. 58(3):892–898.

Purkerson, M., et al. (1985) Inhibition of thromboxane synthesis ameliorates the progressive kidney disease of rats with subtotal renal ablation. Proc. Natl. Acad. Sci. USA 82:193–197.

Redondo, J., et al. (1986/1987) Potentiation of interleukin–2 activity by levamisole and imidazole. Immunology Letters 14:111–116.

Riess, J. et al. (1987) Design, synthesis and evaluation of fluorocarbons and surfactants for in vivo applications new perfluoroalkylated polyhydroxylated surfactants. Int'l Symposium on Blood Substitutes, Montreal, May 1987.

Riess, J. (1984) Reassessment of criteria for the selection of perfluorochemicals for second–generation blood substitutes: analysis of structure/property relationships. Artificial Organs 8(1):44–56.

Saito, H., et al. (1984) Effects of a selective thromboxane $A_2$ synthetase inhibitor on immune complex glomerulonephritis. Nephron 36:38–45.

Schirmer, W., et al. (1987) Effects of ibuprofen, indomethacin, and imidazole on survival in sepsis. Current Surgery Mar.–Apr. 102–105.

Tai, H.–H. and B. Yuan (1978) On the inhibitory potency of imidazole and its derivatives on thromboxane synthetase. Biochem. Biophys. Res. Commun. 80(1):236–242.

Zipser, R., et al. (1980) Exaggerated prostablandin and thromboxane synthesis in the rabbit with renal renal vein constriction. Circulation Research 47(2):231–237.

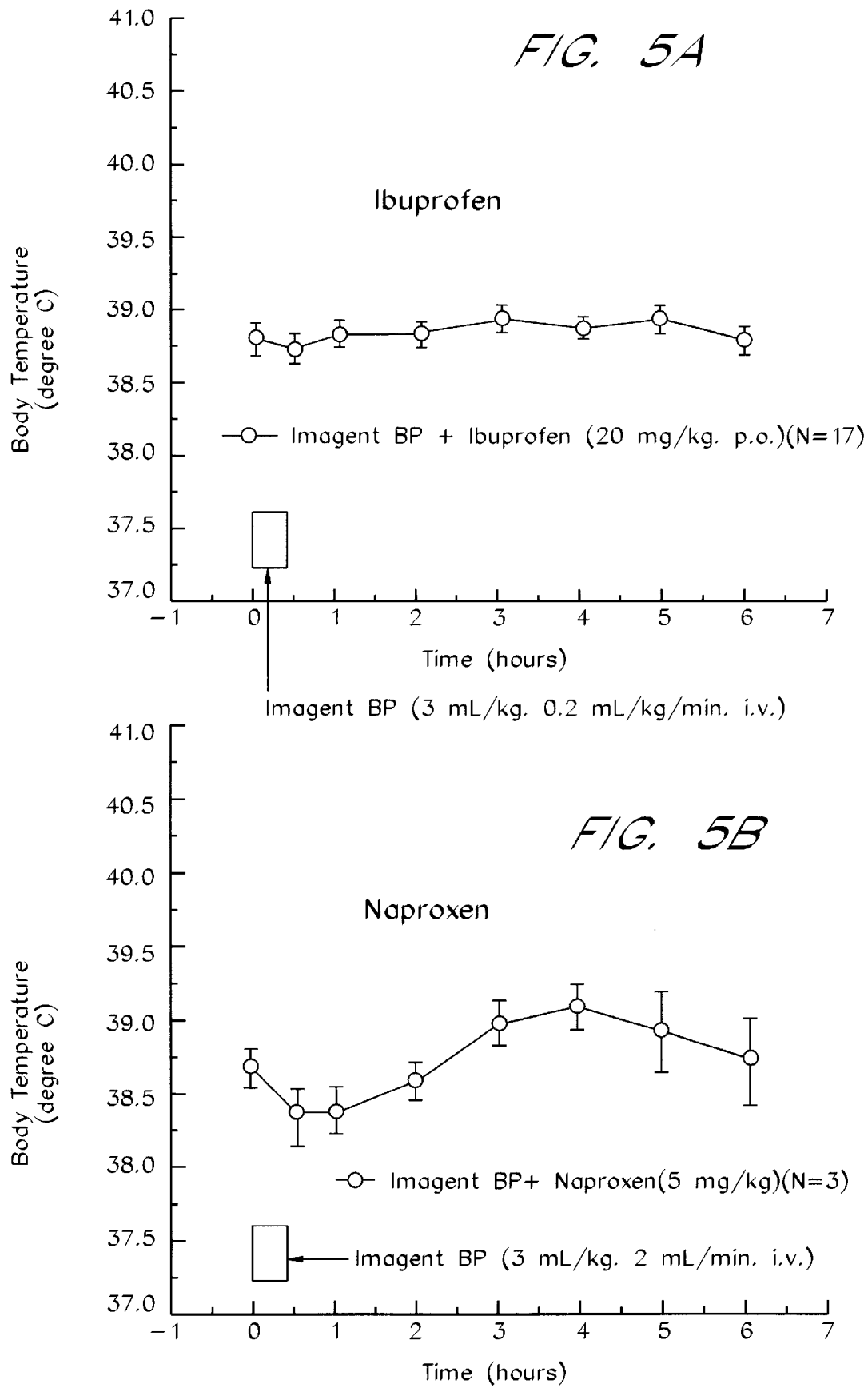

PROPHYLAXIS IN THE PARENTERAL ADMINISTRATION OF PARTICULATE DISPERSIONS IN FLUOROCARBON EMULSIONS

This application is a continuation-in-part of U.S. application Ser. No. 07/417,796, filed Oct. 4, 1989, now U.S. Pat. No. 5,284,645 which is a continuation-in-part of Ser. No. 07/082,846 filed Aug. 5, 1987, now U.S. Pat. No. 4,987,154 which is a continuation-in-part of Ser. No. 818,690, filed Jan. 14, 1986, now U.S. Pat. No. 4,865,836.

This invention relates to the use of therapeutic agents in conjunction with the parenteral administration of lipid dispersions comprising colloidal suspensions of particulate lipids or particulate matter in association with lipid. It relates particularly to the use of therapeutic agents to reduce or eliminate the transient physiological stress reaction observed when fluorocarbon emulsions, emulsified lipids, and liposomal formulations are administered in vivo.

Fluorocarbon emulsions have many useful applications in medicine as intravascular and extravascular imaging or contrast agents. Also, the capacity of fluorocarbons to dissolve high concentrations of oxygen make them suitable as temporary red blood cell substitutes and as oxygen transport agents in the treatment of local ischemia. Frequently, however, the intravascular administration of fluorocarbon emulsions, and other agents comprising lipid dispersions, is accompanied by a mild transient systemic inflammatory and febrile response. The response is usually innocuous, and can be in many respects, beneficial; however, it can cause a period of discomfort for the recipient.

Several sources of physiological stress that occur during the administration of the lipid dispersions described, including the macrophage phagocytosis of particles, as well as the stress provoked by reduced oxygen tension, interrupted blood flow, or infection, can elicit a transient inflammatory response. The response is physiologically and biochemically mediated by the metabolic products of arachidonic acid, i.e., prostaglandins, thromboxane, and leukotrienes.

The biosynthesis of prostaglandins and thromboxane begins with the conversion of free arachidonic acid to an endoperoxide prostaglandin intermediate, $PGH_2$, by means of a cyclooxygenase enzyme. $PGH_2$ is then made available as the precursor for several end product prostanoids. Among these prostanoids are prostacyclin, $PGI_2$, formation of which is catalyzed by prostacyclin synthetase; the active prostaglandins $PGF_{2\alpha}$, $PGE_2$, and PGD; and the thromboxane, $TxA_2$, the formation of which is catalyzed by thromboxane synthetase.

The prostaglandin and thromboxane end products have various effects on cells, but primarily act on macrophages and platelets to release other substances that in turn mediate an inflammatory response characterized by infiltration of the tissues with neutrophils, deposition of immune complexes, edema, and pain.

The prostanoids can have effects that oppose each other; for example, $PGI_2$ and $TxA_2$, the biologically most active of the prostanoids, exert opposite vasoactive and hemodynamic effects: $PGI_2$ is a potent vasodilator and inhibitor of platelet aggregation, whereas $TxA_2$ is a vasoconstrictor and promoter of platelet aggregation.

Various agents are known to inhibit or attenuate the biological activity of prostaglandins and thromboxane. Imidazole, a compound related to the naturally occurring amino acid histidine, inhibits thromboxane synthetase and prevents the synthesis of $TxA_2$; other agents, such as aspirin, ibuprofen, and indomethacin inhibit cyclooxygenase, thus preventing the synthesis of all the prostanoids.

Macrophage phagocytosis not only triggers the release of arachidonate metabolites, but also the release of cytokines such as interleukin-1 (IL-1), interleukin-6 (IL-6) and tumor necrosis factor (TNF). These substances are known to elicit a febrile response via a mechanism of induced local release of prostaglandins in the hypothalamus of the brain. Corticosteroids, e.g., dexamethasone, can inhibit and down-regulate the release of cytokines from macrophages, and cyclooxygenase inhibitors, e.g., ibuprofen, can inhibit the formation of prostaglandins in the hypothalamus.

It would be advantageous to prevent the undesirable transient effects observed during the intravenous administration of lipid dispersions. Accordingly, it is an object of the invention to provide methods to prevent or ameliorate these effects by use of an agent which prevents a systemic inflammatory or febrile response by inhibiting the synthesis of prostaglandins, thromboxane and cytokines, or preventing their release from macrophages.

It is also an object of the invention to provide methods to prevent these adverse effects by the use of other agents which act to suppress an inflammatory or febrile response.

SUMMARY OF THE INVENTION

According to the invention there is provided a method for reducing the Transient Adverse Physiological Response (TAPR) in an animal to parenterally administered particulate dispersions, comprising the steps of administering an anti-inflammatory drug prophylactically to an animal in need thereof in an amount sufficient to oppose the TAPR response; and then administering said particulate dispersion parenterally to a patient. The method is an improvement over previous procedures of administering particulate dispersions, wherein the improvement comprises a prophylactic administration of an anti-inflammatory drug so as to prevent or ameliorate the symptoms of a transient adverse physiological reaction (TAPR) to the particulate dispersion which occasionally occurs, significantly in humans.

The particulate dispersion can comprise, for example, a dispersed lipid, fluorocarbon, or an emulsified triglyceride. The particulate dispersion can also be a liposomal formulation.

According to the method described, the prophylactic drug may be a corticosteroid; preferably the corticosteroid is dexamethasone or methylprednisone. Alternatively, the prophylactic anti-inflammatory drug is a cyclooxygenase inhibitor, a phospholipase A2 inhibitor, or an agent that otherwise inhibits the synthesis of prostaglandins and thromboxane. In one preferred embodiment, the cyclo-oxygenase inhibitor is chosen from the group consisting of indomethacin, ibuprofen, aspirin, and naproxen.

In the application of the method, the dose of the prophylactic anti-inflammatory drug is administered from 30 minutes to 24 hours prior to the procedure of injecting a particulate dispersion into an animal. The prophylactic drug can be administered in two or more doses. The method also comprises the further step of administering the prophylactic anti-inflammatory drug, either continuously or at intervals of time during and after the injection of a particulate dispersion into an animal.

The invention also includes fluorocarbon emulsions comprising an effective concentration of an agent that opposes the TAPR response, selected from the group consisting of steroidal and non-steroidal anti-inflammatory agents, anti-pyretic agents, and non-narcotic analgesics. The emulsion can, for example, comprise an effective TAPR-opposing amount of indomethacin, ibuprofen, naproxen, or combinations thereof. The anti-inflammatory agent can be aspirin, other salicylates, drugs having an imidazoyl group, or any of the non-steroidal anti-inflammatory agents of the various chemical classes disclosed herein. Alternatively, the emulsion can comprise an effective TAPR-opposing amount of a corticosteroid. In preferred embodiments, the corticosteroid can be dexamethasone or methylprednisone.

BRIEF DESCRIPTION OF THE DRAWINGS

FIG. 5 demonstrates the effect of cyclooxygenase inhibitors in opposing the febrile symptoms of the TAPR response to fluorocarbon emulsion (Imagent®BP) in conscious swine: (a) oral ibuprofen, 20 mg/kg, administered 1 h before injection; (b) oral naproxen, 5 mg/kg, administered 1 h before injection.

Figure 1A:
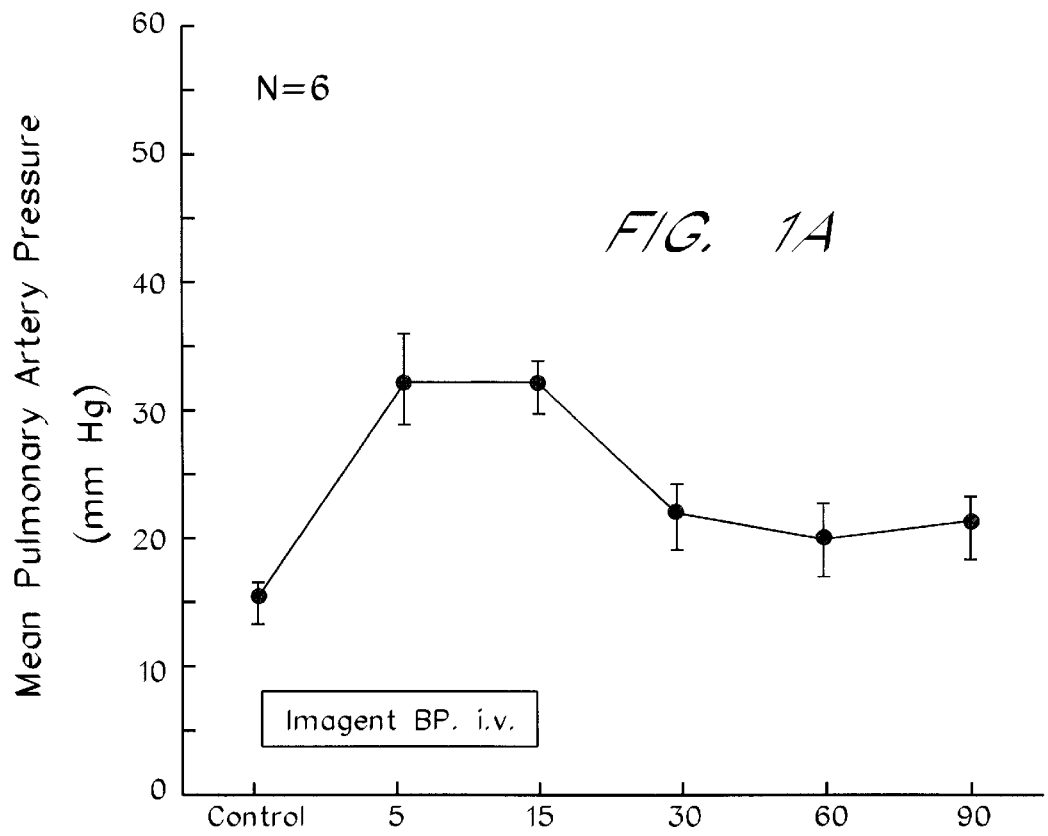
FIG. 1 demonstrates the Transient Adverse Physiological Response (TAPR) to particulate lipid on administration of 90 perfluorooctylbromide emulsion (Imagent®BP) to anesthetized swine: (a) increase in mean pulmonary arterial pressure; (b) relative skin color; (c) cardiac output.

In all of the figures, data are represented as the mean ±standard error of the mean (N=number of animals tested).

DETAILED DESCRIPTION OF THE INVENTION

The present invention provides methods of preventing or ameliorating the symptoms of an undesirable physiological response which frequently accompanies the parenteral administration of lipid dispersions by the prophylactic administration of therapeutic drugs which act to oppose the response in patients receiving such treatment.

Definitions:

A lipid as described herein is any hydrophobic substance of a fatty, oily, or waxy consistency, extractable in nonpolar organic solvents, for example, ethers or chloroform, such substances including fatty acids, their esters and alcohols, phospholipids, mono-, di-, and triglycerides of the fatty acids (fats), sterols, and waxes, whether of natural origin, from mineral, vegetable, or animal sources, or synthetic compounds, alone or in combination with nonlipid substances or other lipid species.

A particulate dispersion as described herein is any system comprising a suspension of particles, and from about 1 nanometer to about 7 microns in size, such dispersions being, for example, liquid/air (aerosols); solid/solid; liquid/liquid (emulsions); or gas/liquid (foams). Lipid dispersions that are emulsions include those having a continuous aqueous phase wherein a lipid emulsifying agent is used to coat particles. Lipid dispersions also include liposomal preparations, comprising unilammelar or multilammelar lipid vesicles, made up at least in part of an amphipathic lipid such as a phospholipid, in suspension in an aqueous medium.

Fluid therapeutic agents comprising dispersed lipid particles or dispersed lipid-coated particles are parenterally administered to patients in a variety of medical regimens. Common lipid dispersions in therapeutic use in humans include, for example, emulsions of radiopaque compounds used as contrast media in diagnostic radiography, emulsions of fats used as nutritive infusions, liposomal formulations comprising lipid-encapsulated bioactive agents; lipids such as lipid A used as immunostimulating adjuvants, or the waxy or oily layers of biodegradable or bioerodible material into which therapeutic agents have been incorporated for delayed or metered release.

Fluorocarbons have the capacity to dissolve oxygen and are therefore useful as transport agents to supply oxygen to ischemic tissues in the body. Other physical properties of brominated or iodinated fluorocarbons make them useful as contrast agents for radiography, computer assisted tomography (CAT scan), ultrasonography, and magnetic resonance imaging (MRI). Fluorocarbon compounds are hydrophobic and are therefore immiscible with body fluids. Emulsification makes it possible to introduce these substances into the circulatory system of the body in a readily dispersible form in which the fluorocarbon droplets are coated with an amphipathic substance which is commonly lipid in nature.

The present invention comprises methods for prophylaxis of the inflammatory response that can accompany the parenteral administration of fluorocarbon emulsions. These emulsions can be made up of an appropriate fluorocarbon, an aqueous phase, and an emulsifying agent. The emulsion can be maintained within a defined pH range by a buffer, for example, an amino acid, phosphate buffer, or other physiologically suitable buffer.

Fluorocarbon molecules used in these emulsions may have various structures, either straight or branched chain or cyclic, as described in Riess, J., Artificial organs 8(1):44–56 (1984). These molecules may also have some degree of unsaturation, and may also contain bromine or hydrogen atoms, or they may be amine derivatives. The fluorocarbons may be present in the emulsion in useful concentrations ranging from about 20% to 125% weight per volume (w/v). As used throughout, concentrations defined as weight/volume are understood to represent grams/ml and % weight per volume to represent grams/100 ml.

Emulsifying agents may be anionic, cationic or nonionic surfactants or combinations thereof as are well known to those in the chemical arts, or they may be mixtures of synthetic compounds such as Pluronic F-68™, a condensate of ethylene oxide with propylene glycol, as used in U.S. Pat. No. 4,073,879 to Long. Fluorosurfactants, such as those described by J. Riess et al., Int'l Symposium on Blood Substitutes, Montreal, May, 1987, are particularly suitable and can also be used. Emulsifying agents may also be mixtures of the above agents. Alternatively, emulsifiers may be natural amphipathic compounds such as phospholipids, particularly the phosphatidylcholines, wherein combined hydrophilic and hydrophobic properties enable the molecule to interface with both aqueous and fluorocarbon systems, thereby forming the emulsion droplets. There are various species of each class of phospholipids, such as the phosphatidyl-cholines, comprising various pairings of saturated and unsaturated fatty acids in the glycerol structures. Phosphatidylcholines are an abundant natural material (lecithin) which may be purified from egg yolk, or may be produced synthetically (Avanti Polar Lipids, Pelham, Ala.).

The phospholipid emulsifying agent is included in the emulsion, usually in the range of 2 to 14% w/v, increasing in proportion to the fluorocarbon concentration. The preferred amount of phospholipid is 2.5 to 5% w/v for an emulsion comprising 75% w/v bromofluorocarbon and 3.5 to 10% w/v of phospholipid for an emulsion with 100% w/v bromo-fluorocarbon. In a preferred embodiment, the phospholipid comprises at least 2% w/v of the emulsion.

Fluorocarbon emulsification may be carried out generally by processes which provide energy to the system to break up the fluorocarbon volume into small droplets of lipid coated fluorocarbon dispersed in an aqueous medium. In a sonication emulsification process, bursts of energy are released from the tip of a probe inserted into mixed emulsion components. In a mechanical emulsification process, such as performed by a Microfluidizer™ apparatus (Microfluidics, Newton, Mass. 02164), energy is supplied by mechanical stress applied to the fluid emulsion components.

The aqueous phase of the emulsion may have components dissolved therein which give the emulsions desirable physiological properties. For example, it may comprise an osmotic agent to bring the emulsion to physiological isotonicity. The osmotic agent may be sodium chloride, or it may be a polyhydroxyl compound, such as a sugar or mannitol. The aqueous phase will also contain soluble buffering agents.

Emulsions having various concentrations of fluorocarbon are useful in different applications, for example, when used as contrast media, for treating ischemia, or when applied intravascularly or within cavities of the body. Accordingly, useful formulations will include those having fluorocarbon concentrations in ranges equal to or greater than 20 to 125%, preferably 40 to 100%, most preferably 60 to 80%. Preferred fluorocarbon emulsion formulations are those disclosed in U.S. Pat. Nos. 4,865,836; 4,987,154; 4,927,623; and 4,951,673 (D. M. Long, Jr.), which are hereby incorporated by reference. The higher concentration emulsions are desirable for their efficiency in transporting oxygen or when used intravascularly to provide contrast for radiographic studies. Low concentration emulsions may be useful in imaging large body volumes. Fluorocarbon concentrations in emulsions are limited by the capacity of the emulsifying agent used, the efficiency of the emulsification process, and by a limiting viscosity.

Transient Adverse Physiological Response (TAPR) to the Intravenous Administration of Lipid Dispersions Occasionally, human patients receiving fluorocarbon emulsions intravenously experience transient "flu"-like symptoms, comprising mild chills or fever, anorexia or nausea, myalgia, particularly as lower back pain, and general malaise. To extrapolate that response to and from animals, we have observed that the intravenous administration of fluorocarbon emulsions to swine provokes an exaggerated, but predictable, physiological response comprising hemodynamic changes, an inflammatory response, and fever. The hemodynamic changes comprise an increase in mean pulmonary artery pressure, an increase in pulmonary vascular resistance, and a slight decrease in cardiac output. These exaggerated and consistent hemodynamic changes are peculiar to species belonging to the order Artiodactyla, and do not occur predictably in other animal species. These effects, together with the inflammatory response evidenced by flushing of the skin, are attributed primarily to activation of the cyclooxygenase pathway of the arachidonic acid cascade. A swine receiving a fluorocarbon emulsion injection also experiences a febrile response attributed to local hypothalamic release of prostaglandins.

The reaction of mammalian species belonging to the order Artiodactyla (sheep, goat, ox and swine) to injections of polystyrene microspheres, fat emulsions (Intralipid®), liposomes, and gram negative organisms has been clearly demonstrated. There is clinical evidence that human subjects respond to the parenteral introduction of lipid dispersions with symptoms analogous to those observed in swine. The intravenous infusion of nutritive 10% and 20% soybean oil fat emulsions, comprising neutral triglycerides and phospholipids in emulsified fat particles approximately 0.5 microns in size, into humans is found to produce symptoms of dyspnea, cyanosis, nausea, vomiting, headache, flushing, fever, sweating, drowsiness, and vertigo in about 1% of patients. (Intralipid® product inserts 716013-1, 716023-1, (August, 1988), Kabivitrum, Inc. Alameda, Calif. 94501). Almost 20% of patients experienced one or many of symptoms comprising chills, rigor, fever, sinusitis, jaw pain, malaise, nausea, dizziness, urticaria, periorbital edema, and itching eyes after receiving intravenous injections of iodinated poppy seed oil (EOE-13), in emulsified particles 1–4 microns in size, with a mean diameter of 1.7 microns, as a contrast agent for computerized tomography [CT], (Miller, D. et al., American Journal of Radiology 143:235–243 (1984). The placebo group in a study of the administration of a colloidal dispersion of amphotericin B/cholesterol sulfate formulations experienced headache and nausea (Guo, L. et al., as reported in *Liposomes in Drug Delivery: 21 Years On,* The School of Pharmacy, University of London, 12th–15th Dec. 1990).

We have designated the responses of swine to parenteral injection of fluorocarbon emulsions a Transient Adverse Physiological Response (TAPR). It is believed that the observed human response to fluorocarbon emulsions, even though different, is mediated through the same mechanism: that of the TAPR observed in swine. Further, based on the evidence that (a) the TAPR response to parenteral fluorocarbon emulsions parallels the response to parenteral lipid emulsions in both swine and humans, such reactions varying only in severity and duration; (b) the TAPR of swine to parenteral fluorocarbon emulsions is independent of fluorocarbon concentration or total dose; and (c) control groups in studies of liposomal therapy in humans, who presumably receive only empty liposomes (Guo et al., supra), also experience a TAPR-like response, the previously unrecognized provoking agent is the particulate lipid component itself. All are inflammatory responses arising from identical physiological and biochemical mechanisms, and for that reason the analogous response seen in response to the administration of other types of lipid dispersions in both species, is amenable to the same therapy and prophylaxis as that for the administration of fluorocarbon emulsions according to the methods of the invention.

Prophylaxis for the Acute and Delayed TAPR Response to Fluorocarbon Emulsions and Other Lipid Dispersions The TAPR response of humans and other animals to the administration of fluorocarbon emulsions and other lipid dispersions as described above comprises both an acute transient reaction and a delayed reaction. The acute transient reaction of the swine to the intravenous administration of fluorocarbon emulsions comprises a rise in pulmonary artery pressure which may be accompanied by a slight increase in respiratory rate and a flushing of the skin; in human and other species the acute response includes flushing and lower backache. The delayed response in most species is febrile in nature and is not accompanied by any hemodynamic change.

Both the acute and delayed reactions can be prevented or ameliorated by prophylactic treatment with drugs that block the action of cyclooxygenase and prevent the activation of the arachidonic acid cascade. Both reactions can also be prevented or ameliorated by prophylactic treatment with steroids. Prophylaxis provides a preferred therapeutic management of both the immediate and delayed response because it allows the dosage of the patient according to his needs and independent of the fluorocarbon emulsion composition or rate of administration. However, a prophylactic approach to TAPR can be combined with co-administration of anti-inflammatory agents together with the fluorocarbon emulsion, as demonstrated in the following examples.

Domestic swine (10–20 kg) were used as models to study the response to fluorocarbon emulsions, based on the substantial body of published research regarding the sensitivity of the species to particulate injections. The primary response is a rapid and substantial rise in pulmonary vascular resistance and in some animals a significant degree of skin flushing. We have discovered that the mechanism of these responses is related to the particle-induced activation of pulmonary intravascular macrophages which reside in vast numbers on the endothelial lining of the pulmonary circulation in these species and is therefore not specific to fluorocarbon emulsions. Upon activation and as a part of the normal phagocytic response to foreign particles, these cells generate substantial quantities of prostaglandins and thromboxane secondary to the stimulation of the arachidonic acid cascade. Thromboxane in particular is a potent agonist in pulmonary vascular smooth muscle and will cause substantial increases in pulmonary vascular resistance. Prostaglandins (i.e. prostaglandin $D_2$) are thought to cause the skin flushing reaction that is associated with the vitamin, niacin.

When swine were administered fluorocarbon emulsions, as described in Example 1, physiological responses similar to those known for the particulate injections described above were observed, comprising an increase in pulmonary arterial pressure, a decrease in cardiac output, and skin flushing. The effect was independent of the concentration of fluorocarbon in the emulsions, in view of the finding that both 20% Fluosol® and 90 to 100% Imagent® (Alliance Pharmaceutical Corp., San Diego, Calif. 92121) caused similar hemodynamic changes in the swine model. These responses were transient and were resolved by 2 hours post injection. Both responses are attributed primarily to products of the arachidonic acid cascade. Plasma samples taken at the beginning and during the course of the intravenous injection indicated no increases in levels of histamine, serotonin, or bradykinin.

Figure 4A:
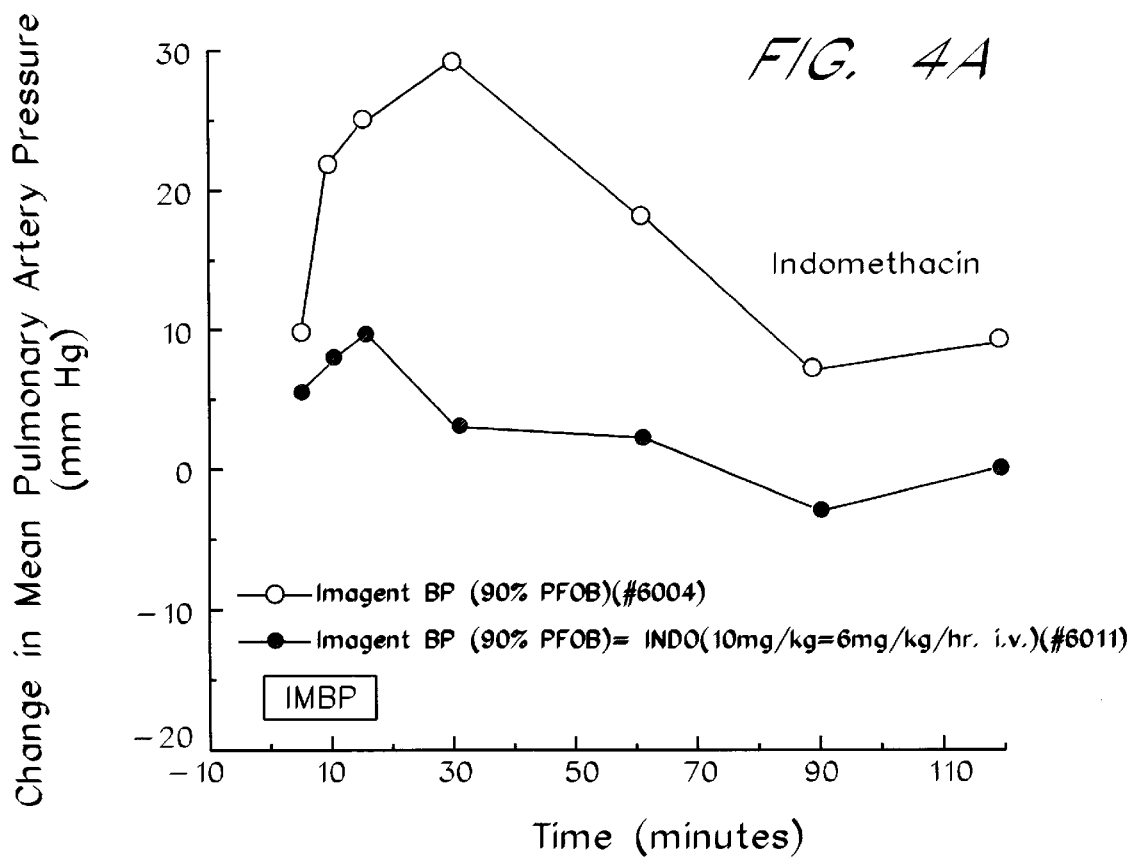
FIG. 4 demonstrates the effect of cyclooxygenase inhibitors in opposing the fluorocarbon (Imagent®BP) induced rise in mean pulmonary arterial pressure in anesthetized swine: (a) intravenous indomethacin (INDO); (b) oral ibuprofen, 1 h before injection; (c) oral aspirin, 1 h before injection.
Figure 4B:
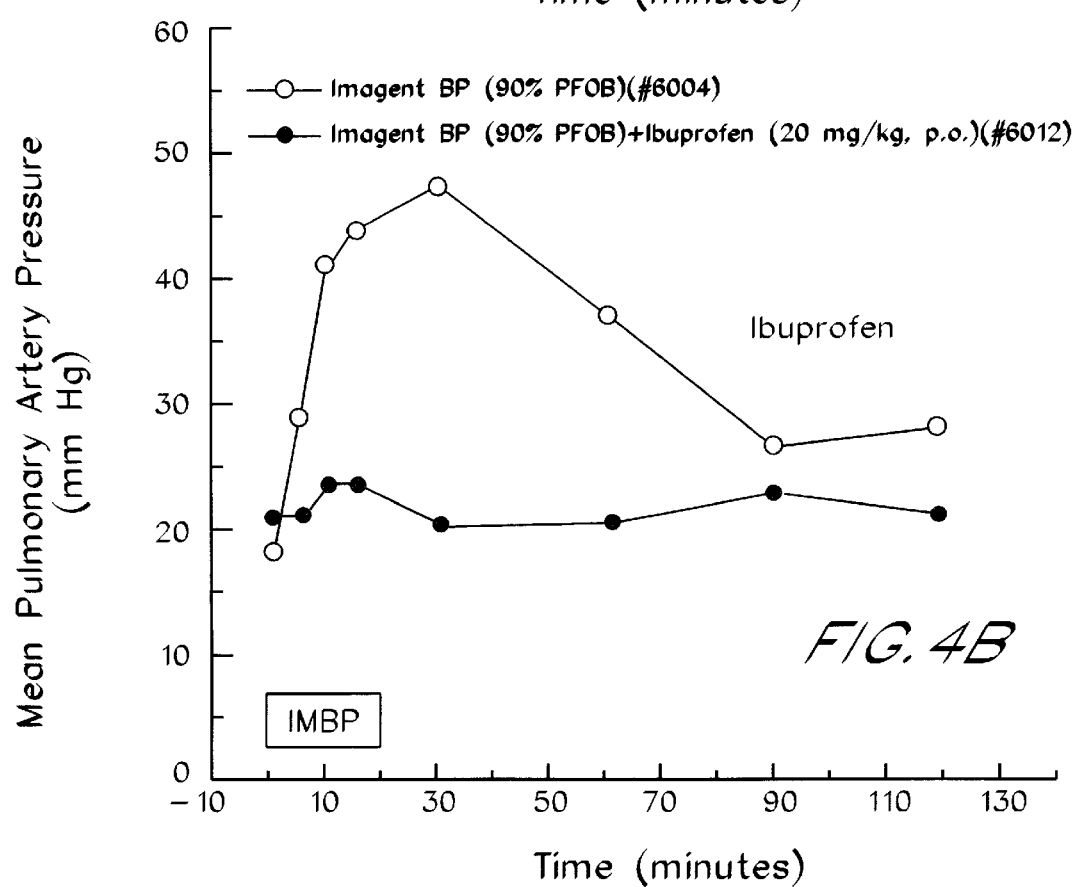
Figure 4C:
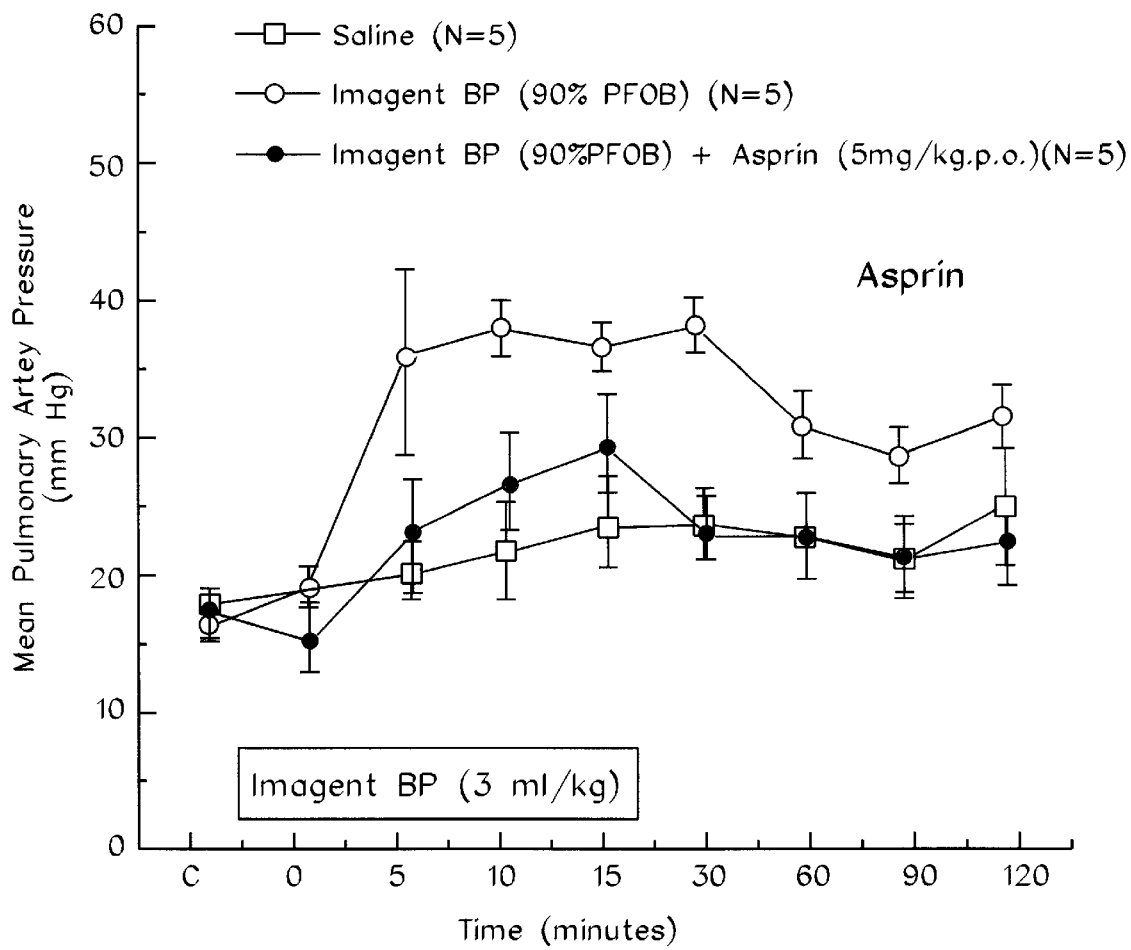

The prophylactic administration of cyclooxygenase inhibitors, including intravenous indomethacin, oral ibuprofen, and oral aspirin, was found to prevent the acute hemodynamic response to fluorocarbon emulsions in anesthetized swine as indicated by increases in mean pulmonary artery pressure (Example 2; FIGS. 4(a), 4(b), 4(c)).

Swine also respond to fluorocarbon emulsion injections with a delayed febrile response. At approximately 2 hours post injection, there is a rise in core body temperature (Example 3) which continues for up to 6 hours post injection. There are no accompanying hemodynamic or hematological changes. The results indicate that cyclooxygenase inhibitors also block this observed delayed febrile response. The febrile reaction is not prevented by prophylactic treatment with aspirin or acetaminophen, but was significantly suppressed by prophylactic doses of ibuprofen, and attenuated by prophylactic doses of naproxen (a propionic acid derivative), FIGS. 5(a) and 5(b). Differences in efficacy among various specific drugs are correlated with plasma half-life. The active cyclooxygenase-inhibiting moiety of aspirin, acetylsalicylic acid, has a plasma half-life of 0.25 ±0.03 hrs; ibuprofen, the more efficacious agent, has a longer half-life of 2+0.5 hrs. While naproxen has a greater potency and longer plasma half-life than ibuprofen, its rate of oral absorption is influenced by the presence of food in the stomach, and is therefore difficult to achieve effective plasma levels of this drug by means of orally administered therapy.

Figure 6A:
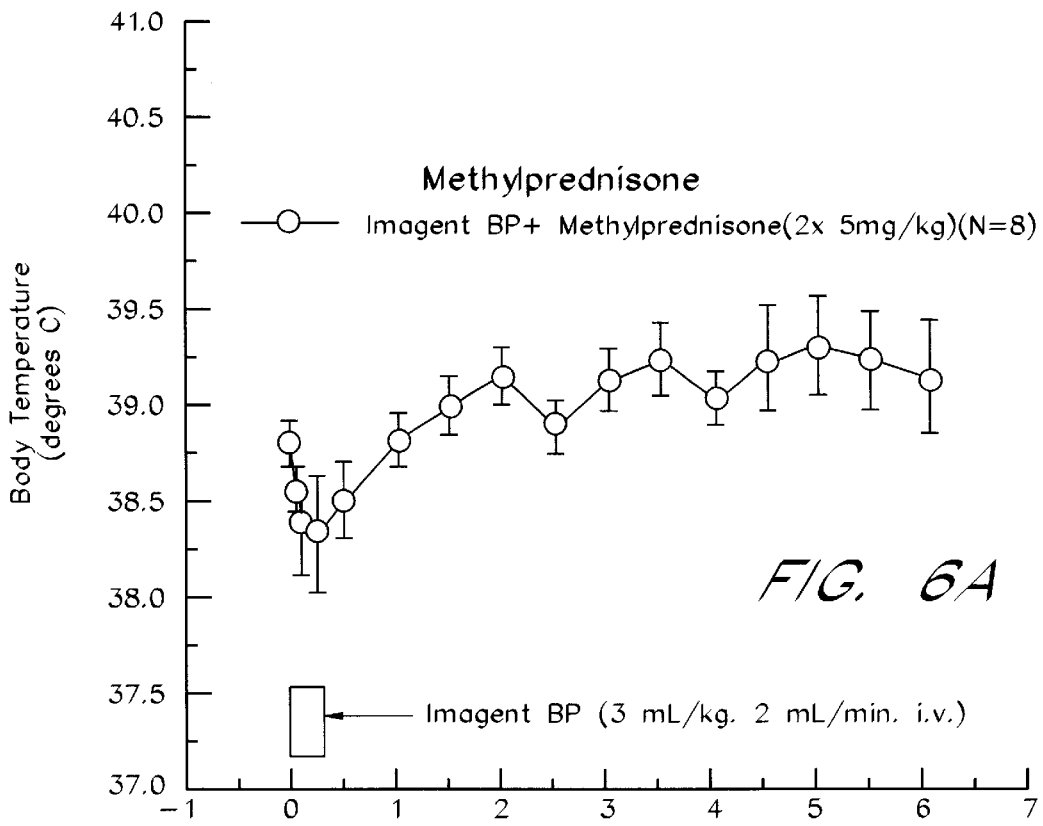
FIG. 6 demonstrates the effect of corticosteroids in opposing the febrile symptoms of the TAPR response to fluorocarbon emulsion (Imagent®BP) in conscious swine: (a) oral methylprednisone, 5 mg/kg, administered 12 h and 2 h before injection; (b) oral dexamethasone, 1 mg/kg, administered 12 h and 2 h before injection.
Figure 6B:
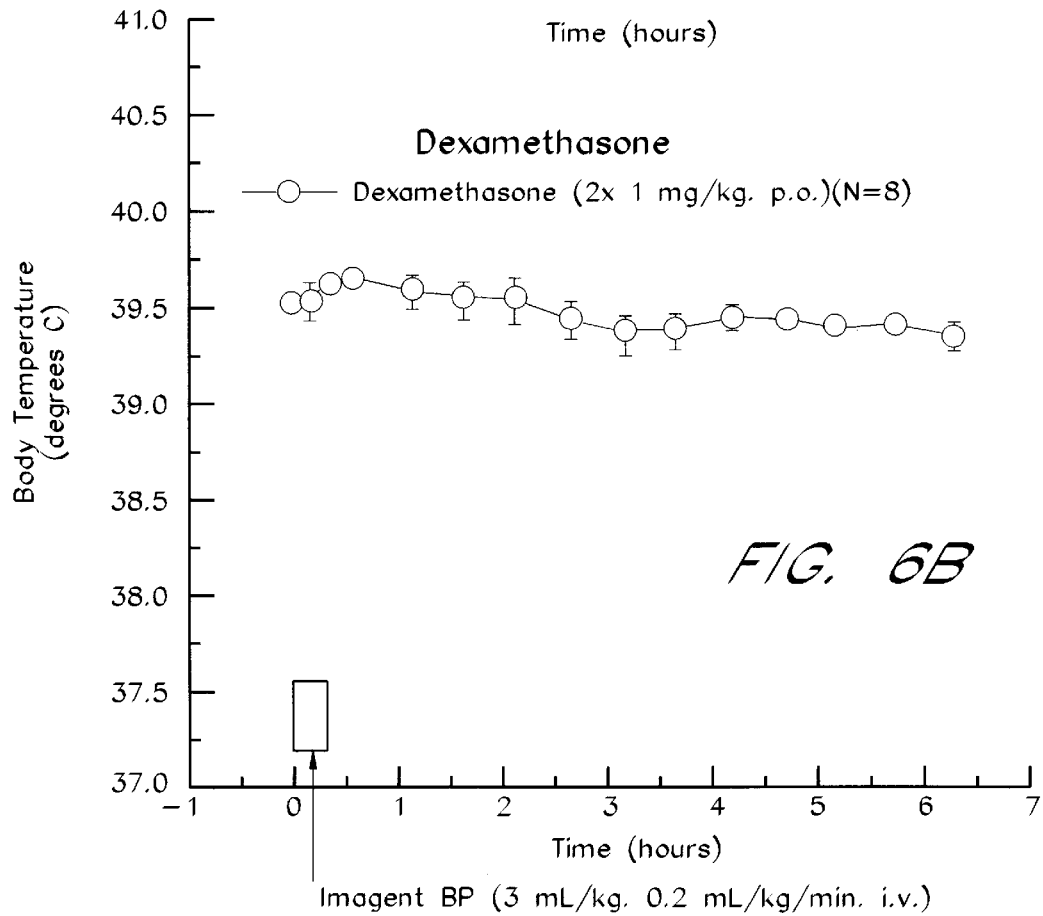

The delayed febrile response is also effectively blocked by means of prophylactic treatment with steroids (Example 3B). Methylprednisone, FIG. 6(a), attenuates the response, whereas dexamethasone, FIG. 6(b), effectively suppresses or eliminates the response.

Other therapeutic agents are effective in treating the TAPR response described. One amino acid derivative, imidazole, a nitrogen containing cyclic radical present in the side chain of the amino acid histidine, has therapeutic properties which ameliorate the hemodynamic and inflammatory responses of subjects. The therapeutic effects of imidazole appear to flow from a number of physiological mechanisms. One theory of mechanism, underlying its anti-inflammatory effect, is related to its ability to inhibit the production of thromboxane.

For all the reasons stated above, adverse responses of the TAPR type to the administration of any lipid dispersion, including fat emulsions provided parenterally for nutritive purposes or parenteral liposomal therapies, can accordingly be treated or prevented according to the methods of the invention in a manner identical to that disclosed for treating the response to fluorocarbon emulsions.

The method generally comprises administering a prophylactic dose of a therapeutic drug of the types or classes described within a period of time before the injection of fluorocarbon emulsion or other lipid dispersion begins. In preferred applications, the administration of the anti-inflammatory agent is continued throughout the injection of the agent.

Anti-inflammatory therapeutic drugs can be administered orally, transdermally, or parenterally; i.e., intravenously, intraperitoneally, and the like, and in any dosage form as appropriate: (a) for oral administration, as tablets, capsules, or dissolved or dispersed in a liquid carrier; or (b) for parenteral administration; e.g., dissolved or dispersed in a suitable liquid carrier or emulsified. These drugs are available commercially in clinically useful form, as indicated above.

Whatever dosage form of the drug is used, the amount of the anti-inflammatory compound administered in humans should be sufficient to effect a substantial mitigation of the adverse hemodynamic and febrile responses associated with fluorocarbon emulsions in vivo. Generally, the effective dose can be estimated from the manufacturer's indicated dose on the product insert or on effective doses reported in pharmacology references, such as, for example, Goodman and Gilman, *The Pharmacological Basis of Therapeutics* MacMillan, New York, 1976; especially Chap. 17, Analgesic-Antipyretics, p. 314, and Chap. 72, Adrenocortical Steroids, p. 1604; or *The Physicians' Desk Reference,*

1991 Edition, Medical Economics Corporation, Oradell, N.J. Preferred ranges for total dose of anti-inflammatory agents to provide prophylaxes for a TAPR-like response are from 0.300 to 3.000 grams of aspirin, 0.200 to 1.600 grams ibuprofen, and 25 mg to 200 mg indomethacin.

Effective prophylactic activity requires that a sufficient level of anti-inflammatory agent be present in the body of the patient before administration of the fluorocarbon emulsion or other lipid dispersion. To achieve the appropriate levels, doses of the drugs are given in the 24 hour period preceding the scheduled procedure. The times and intervals of the premedication schedule are determined by the half-life of the specific drug, according to procedures known to those skilled in the art. Preferred administration schedules for the anti-inflammatory agents are one dose about 1 hour prior to administration of the lipid dispersion and at appropriate intervals thereafter to maintain effective blood levels of the drug. Preferred ranges for total dose of corticosteroids is 5 mg to 100 mg for both prednisone and methylprednisone and 0.5 to 25 mg for dexamethasone. The corticosteroids can be administered preferably in two doses prior to injection of the lipid dispersion, most preferably at 12 hours and 2 hours before the fluorocarbon emulsion is injected, and at appropriate intervals thereafter as appropriate to maintain their effective blood levels. Dosage and schedule may be adjusted or modified according to experience and clinical judgment.

Administration of Anti-inflammatory agents in Conjunction with Lipid Dispersions:

In addition to the prophylactic therapy disclosed above, the TAPR response can be ameliorated by the administration of anti-inflammatory agents incorporated into fluorocarbon emulsions or other lipid dispersions to ameliorate the inflammatory response associated with the administration of these formulations in vivo. This therapy can be carried out either in conjunction with the prophylactic therapy disclosed or it can be used independently.

Copending application Ser. No. 07/417,796 provides fluorocarbon emulsions containing, as a component of formulation, imidazolyl-based anti-inflammatory agents which are inhibitors of thromboxane synthetase, cyclooxygenase, or phosphodiesterase activators. The emulsions may also include other similarly acting agents, for example, aspirin, ibuprofen, and indomethacin. These therapeutic agents are found to reduce the fever, anorexia, and malaise which occur during intravenous administration of fluorocarbon emulsions.

Experimental work indicates that drugs which are imidazole derivatives, such as N(7-carboxyheptyl)imidazole, 1-methyl-imidazole, 4-(2-(1H-imidazol-1-yl)ethoxy) benzoic acid (dazoxiben), and imidazo(1,5-pyridine-5-hexanoic acid) (CGS 13080), (Ciba-Geigy, West Sussex, United Kingdom) act effectively to inhibit thromboxane synthetase in the rat (Maguire, E. and Wallis, R., Thrombosis Research 32:15–27 (1983), and these drugs may be similarly incorporated into fluorocarbon emulsions or other lipid dispersions in comparable concentrations.

It has been found according to the above-referenced application Ser. No. 07/417,796 that symptoms observed in reaction to intravenous administration of fluorocarbon emulsions to tumor-bearing animals can also be alleviated by cyclooxygenase inhibitors such as ibuprofen. Other anti-inflammatory agents, comprising aspirin (acetylsalicylic acid) or other salicylates, indomethacin (1-(P-chlorobenzoyl)-5-methoxy-2-methylindole-3-acetic acid) and ibuprofen ((±)-2-(p-isobutylphenyl)propionic acid) may be added to fluorocarbon emulsions or to imidazole or histidine-containing fluorocarbon emulsions in established therapeutic concentrations to enhance the anti-inflammatory effects thereof. Accordingly, these drugs may be added to fluorocarbon emulsions of the invention in amounts sufficient to establish a total dose of 300 to 5000 mg of aspirin; 200 to 1600 mg of ibuprofen; and 25 to 200 mg of indomethacin.

Other agents are available which inhibit an inflammatory response by potent and selective biological actions. One of these is SQ 29,548, [1S-[1α,2β(5Z),3β,4α]]-7-[3-[[2-[phenylamino)carbonyl]hydrazino]methyl]-7-oxabicyclo[2.2.1]hept-2-yl]-5-heptenoic acid (Squibb Institute for Medical Research, Princeton, N.J.) which acts to inhibit vasoconstriction and platelet aggregation by blockade or antagonism of thromboxane $A_2$ receptors. The pharmacology of SQ 29,548 is described by Ogletree, M. L. et al. Jour. of Pharmacol. and Exper. Therapeutics 234(2):435–441 (1985). Another is LY53857 (Eli Lilly, Indianapolis, Ind.) which acts by blockade or antagonism of serotonin receptors. The action of LY53857 is described in Golino, P. et al. Circulation 79:911–919 (1989). These drugs can therefore be usefully incorporated into the fluorocarbon emulsions of the invention separately or together in doses of about 0.2 mg/kg body weight for each drug.

Further, the fluorocarbon emulsions can comprise several classes of non-steroidal anti-inflammatory agents; for example, those listed in the Merck Index (Eleventh edition, 1989), Merck therapeutic category 15, as derivatives of aminoarylcarboxylic acid; arylacetic acid;arylbutyric acid; arylcarboxylic acid; arylpropionic acid; pyrazoles; pyraxolones; salicylic acid; and thiazinecarboxamides. The emulsions can also comprise non-narcotic analgesics (Merck Therapeutic category 6) known to have anti-inflammatory activity. The dose ranges for parenteral administration of these agents are in some cases well known to those skilled in the art; in other cases, the effective emulsion concentration of the agents can be determined from known effective peak plasma levels and biological half-life data that appears in references such as the Physician's Desk Reference, 13th Edition (1992) published by the Medical Economics Company, at Montvale, N.J. 07645; or in pharmacological textbooks and formularies.

All of the agents found to be efficacious in reducing the inflammatory response to fluorocarbon emulsions can be similarly applied in treating the inflammatory TAPR response that occurs following the administration of other lipid dispersions.

The present invention is described in detail using the following examples; however, the methods described therein are broadly applicable, and are not to be understood as limited thereby in any way whatsoever. In the following examples, all temperatures are set forth uncorrected in degrees Celsius.

EXAMPLE 1

Physiologic Effects of Imagent®BP on Anesthetized Swine and Without Prophylactic Treatment Cardiovascular Response These experiments were initiated in order to examine the cardiovascular effects of Imagent®BP (perfluorooctyl bromide emulsion, Alliance Pharmaceutical, San Diego, Calif. 92121) on domestic swine. The hemodynamic and skin color responses to a standardized intravenous infusion of the test emulsion (with or without prophylaxis) were compared to recent, but historical, responses to saline placebo infusion in young (lokg) white-skinned domestic farm pigs.

Figure 2:
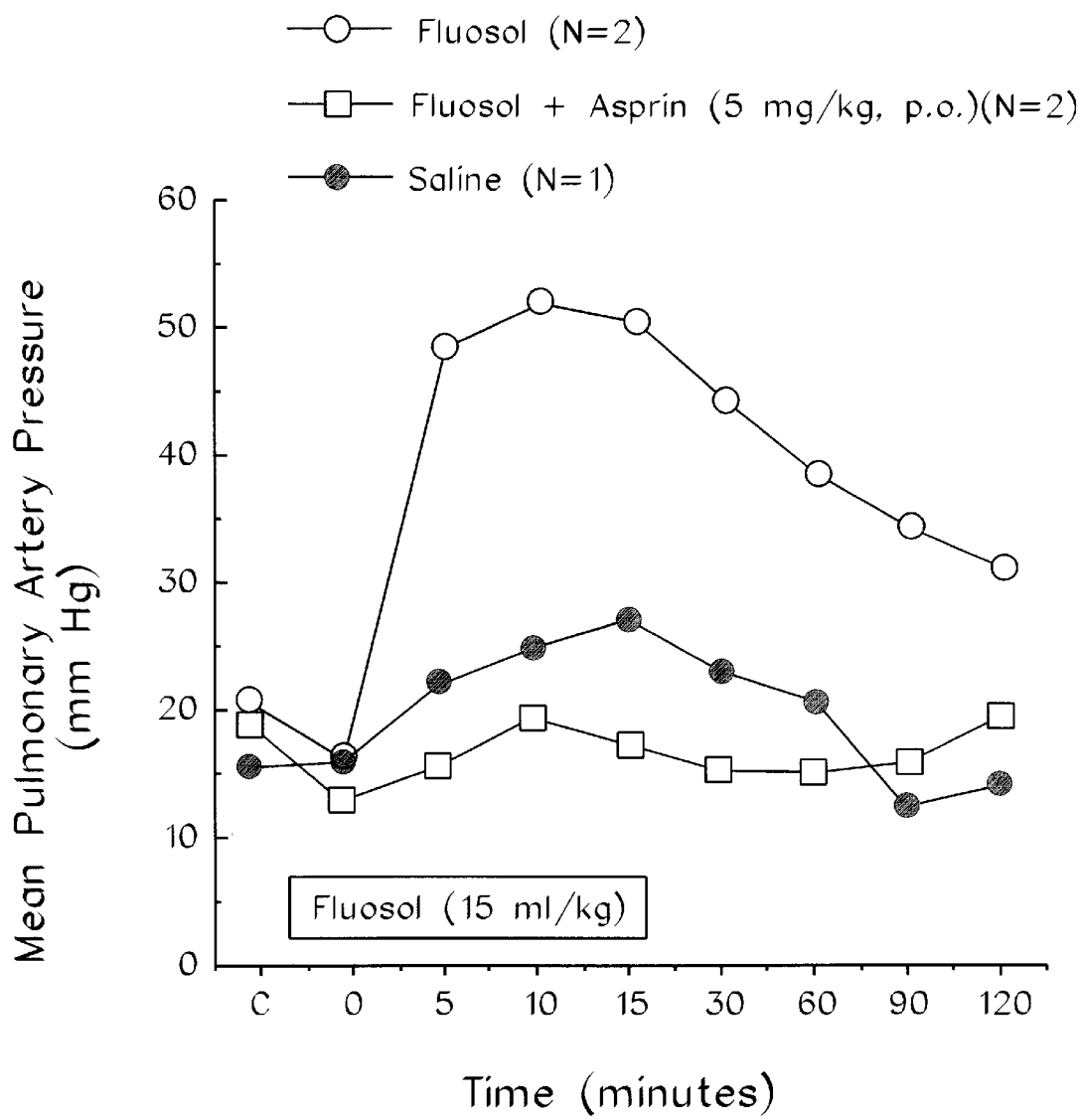
FIG. 2 demonstrates the TAPR response to 20% fluorocarbon emulsion (Fluosol®, Alpha Therapeutics, Los Angeles, Calif.) in anesthetized swine as increased mean pulmonary arterial pressure when administered alone, and compared to a decreased response with aspirin pretreatment.
Figure 3A:
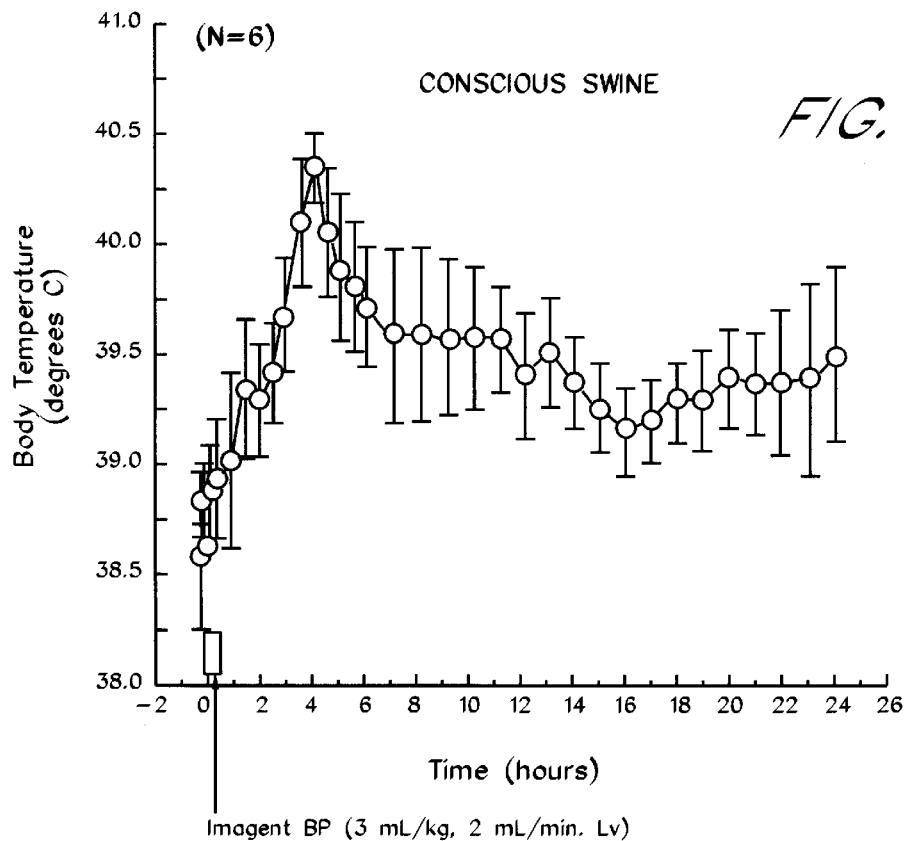
FIG. 3 demonstrates the febrile response of swine to the parenteral injection of lipid dispersions: (a) Imagent®BP; and (b) Intralipid®20%, a 20% I.V. nutritive fat emulsion, comprising neutral triglycerides and phospholipids.
Figure 3B:
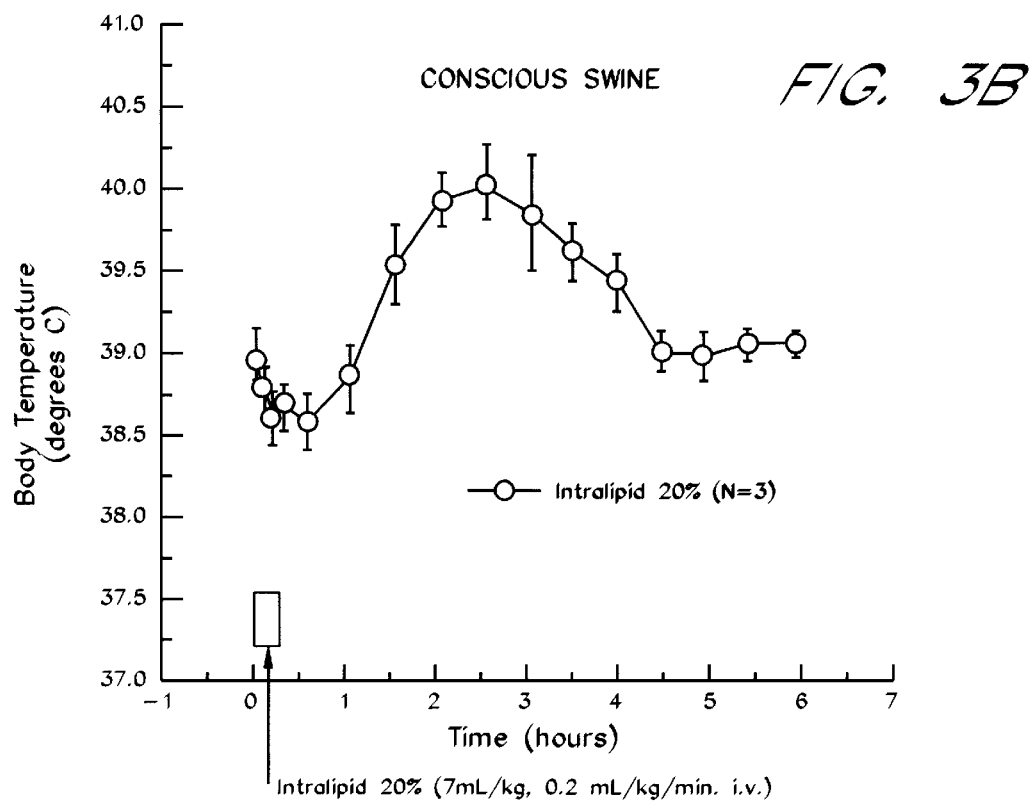

All animals were fully anesthetized (ketamine-sodium pentobarbital), placed on positive pressure ventilation, and instrumented for determination of pulmonary artery pressure, cardiac output, ECG (electrocardiogram), right atrial pressure, and whole blood samples collections. Changes in skin color were also quantified using a relative color scale ranging from normal (light pink) to darker shades of pink and purple. Continuous electrocardiographs and oscillographic recordings of blood pressures were made. At least 30 minutes of baseline data were collected before intravascular administration of the substances. After control recordings, infusion of the pigs was carried out with 3 ml/kg body weight of either fluorocarbon emulsion as Imagent®BP (90% or 100% perfluorooctylbromide) or saline at a rate of 2 ml/min i.v. over 15 minutes. An additional sow was injected with Fluosol®, (Alpha-therapeutics, Irvine, Calif.), 20% fluorocarbon; 3 or 15 ml/kg, 2 ml/min. (FIG. 2, dose of Fluosol® equal in perfluorocarbon dosage to the Imagent®BP dosage).

Data were recorded at 5 minute intervals for the first 15 min, again at 30 minutes, and at 30 minute intervals between 30 and 90 or 120 min. The responses were recorded for a total of 90 minutes after the onset of infusion. Blood samples were drawn before, and 15 to 30 minutes after doses of control, test or reference material. Values for mean pulmonary arterial pressure (mPAP), cardiac output, cardiac index, CBC and skin color were determined.

Figure 1B:
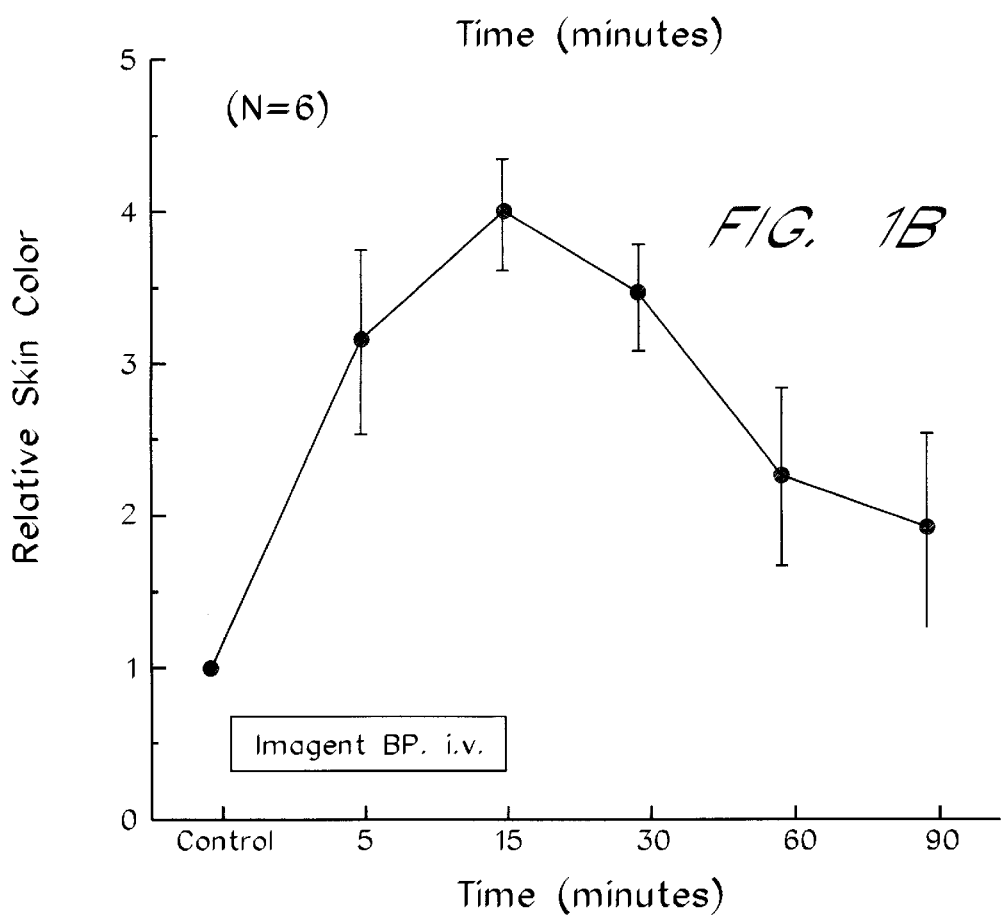
Figure 1C:
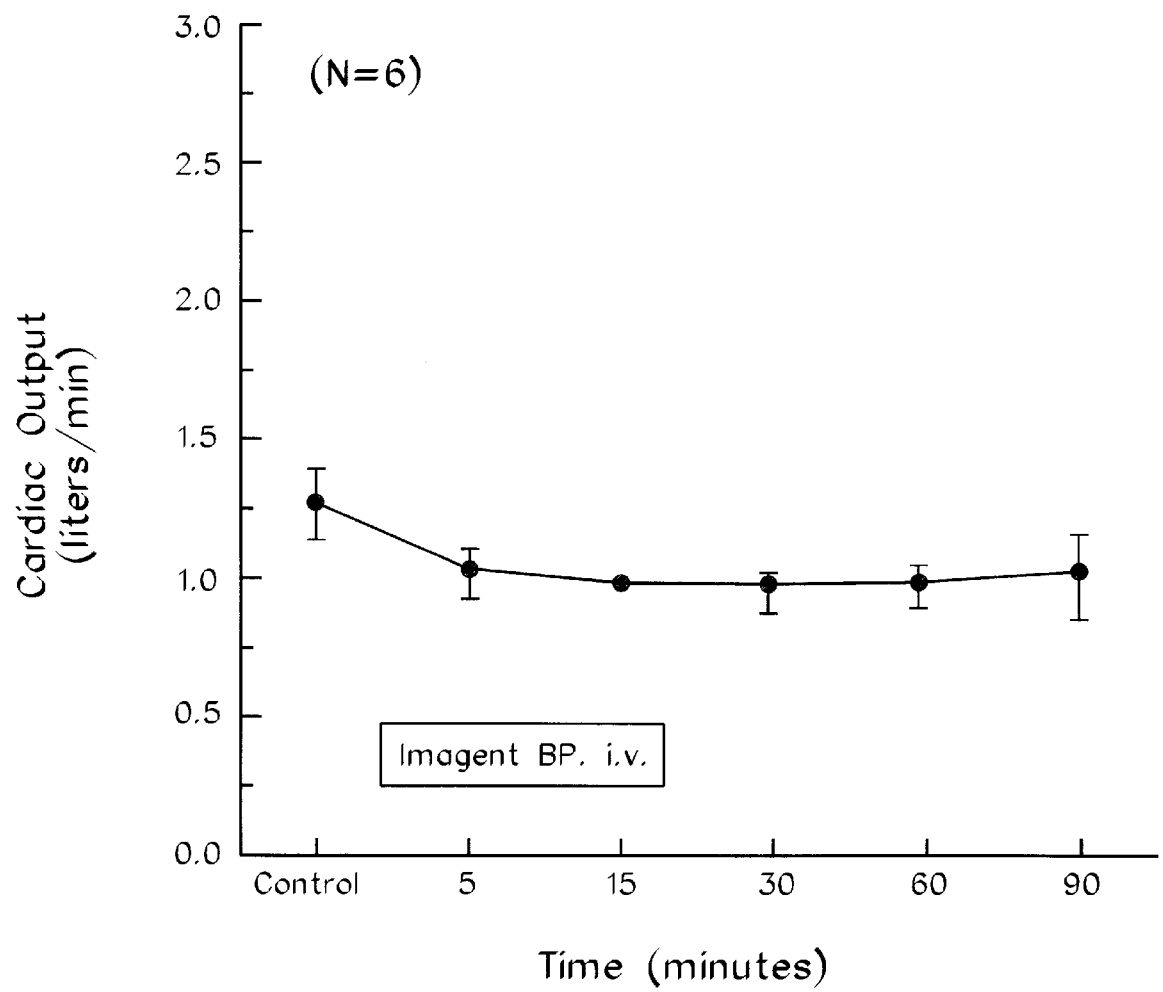

The responses produced by Imagent®BP and not seen in the placebo group included an elevation in mPAP, FIG. 1(a) (systemic arterial blood pressure was unchanged) and a skin flush, FIG. 1(b). Platelet counts rose immediately, and white cell levels increased 90–120 minutes post-infusion. No effect on cardiac output, FIG. 1(c), mean arterial pressure, or heart rate was noted.

The magnitude of the mPAP increments was much greater and more sustained in swine infused with Fluosol® (See FIG. 2) than in the Imagent®BP animals.

EXAMPLE 2

Prophylaxis of the Hemodynamic Response to the Intravenous Injection of Fluorocarbon Emulsions with Cyclooxygenase Inhibitors A series of experiments was conducted to evaluate the effects of prophylactic treatment with cyclooxygenase inhibitors on the acute hemodynamic response to intravenous injection of 90% Imagent®BP in anesthetized swine. Both control and test swine were treated by injection of fluorocarbon emulsion as described in Example 1. Animals receiving prophylaxis were administered indomethacin (0.5 mg/kg p.o.) prior to administration of the test article. Test swine were treated prophylactically with indomethacin, ibuprofen and aspirin. Indomethacin was administered intravenously in an initial bolus of 10 mg/kg followed by a continuous injection of 6 mg/kg/hr over the course of the fluorocarbon injection; Imagent®BP was administered intravenously to the treated animal and to a control for 15 min at a rate of 2 ml/min to a level of 3 ml/kg, FIG. 4(a). Ibuprofen was administered orally to a test animal in a dose of 20 mg/kg and 1 hour later Imagent®BP was administered intravenously to the ibuprofen treated animal and a matching control for 15 min at a rate of 2 ml/min to a level of 3 ml/kg, FIG. 4(b). Aspirin was administered orally at a dose of 5 mg/kg 1 hour prior to Imagent®BP (90%) injection; Imagent®BP was administered intravenously to the aspirin-treated animal and to a matching control at a rate of 2 mL/kg to a level of 3 ml/kg in a period of 15 min, FIG. 4(c).

Premedication with indomethacin virtually prevented all of the hemodynamic reactions in the Imagent®BP treatment groups. Ibuprofen significantly attenuated the mPAP responses, which returned quickly to baseline values. Prophylaxis with aspirin appeared to completely block any increases in mPAP. Aspirin was similarly effective in maintaining the blood cell counts (erythrocytes, leukocytes, platelets) at a level nearly identical to that seen with the saline control.

EXAMPLE 3

Prophylactic Treatment to Block the Febrile Response to Fluorocarbon Emulsion Injection Swine were instrumented 48 hours prior to study for determination of core body temperature using a catheter-tipped thermistor, and for intravenous injection using an axillary vein catheter. On the day of study, core body temperature was determined at baseline and at regular intervals for 6 h after intravenous injection of Imagent®BP. The delayed febrile response to intravenous Imagent®BP (90% perfluorooctylbromide emulsion) was evaluated and compared to an equal volume injection of normal saline. Imagent®BP induced a febrile response which peaked at approximately 3.5 h after initiation of the injection. The peak response constituted nearly a 1° C. rise in core body temperature.

A: Treatment with Cyclooxygenase Inhibitors

In test animals treated prophylactically with ibuprofen at an oral dose of 20 mg/kg, the febrile response was significantly suppressed throughout the 6 h time course FIG. 5(a). In test animals treated prophylactically with naproxen at an oral dose of 5 mg/kg, an attenuated febrile response was observed in comparison to the control group FIG. 5(b).

B: Treatment with Corticosteroids

The delayed febrile response to Imagent®BP was evaluated in conscious swine after prophylactic treatment with two different corticosteroids. Methyl prednisone (5 mg/kg) was administered orally to a set of eight test animals 12 hours and again 2 hours prior to initiation of Imagent®BP injection. Dexamethasone (1 mg/kg) was administered orally to another set of eight animals using the same dose-timing regimen. In the animals receiving methylprednisone, an attenuated febrile response was observed after injection of Imagent®BP, FIG. 6(a); in those animal receiving dexamethasone, the Imagent®BP-induced febrile response was completely blocked FIG. 6(b).

These results suggest that prophylactic treatment with corticosteroids in general and with dexamethasone in particular will effectively suppress or eliminate the emulsion-induced febrile response in conscious swine.

It should be apparent from the foregoing that various other agents may be substituted in the examples to give similar results. Accordingly, the invention may be embodied in other specific forms without departing from it in spirit or essential characteristics. The described embodiments are to be considered in all respects only as illustrative and not to be restrictive, and the scope of the invention is, therefore, indicated by the appended claims rather than by the foregoing description. All modifications which come within the meaning and range of the lawful equivalency of the claims are to be embraced within their scope.

What is claimed is:

1. A method for the parenteral administration of a fluorocarbon emulsion comprising the steps of:

administering prophylactically to a mammal in need of said emulsion, an anti-inflammatory drug in an amount sufficient to oppose the transient adverse (TAPR) response thereto; and administering said emulsion parenterally to said mammal, whereby said transient adverse physiological (TAPR) response is prevented or attenuated.

2. An improvement in a method for parenteral administration of a fluorocarbon emulsion to a mammal in need thereof, wherein the improvement comprises a prophylactic administration of an effective amount of a TAPR-preventing or TAPR-opposing anti-inflammatory drug, wherein the anti-inflammatory drug is administered to the mammal before administration of the fluorocarbon emulsion.

3. A method for the parenteral administration of a fluorocarbon emulsion to a patient in need thereof, comprising in conjunction with said parenteral administration, prophylaxis with an effective anti-inflammatory dose of a drug which acts to oppose the transient adverse physiological (TAPR) response of said patient to said emulsion.

4. The method of any one of claims 1–3, wherein said prophylactic drug is a corticosteroid.

5. The method of claim 4, wherein said drug is dexamethasone or methylprednisone.

6. The method of any one of claims 1–3 wherein said prophylactic drug is a phospholipase-A2 inhibitor.

7. The method of any one of claims 1–3, wherein said prophylactic drug is a cyclooxygenase inhibitor, or otherwise inhibits the synthesis of prostaglandins and/or thromboxane.

8. The method of claim 7, wherein said drug is chosen from the group consisting of indomethacin, ibuprofen, aspirin, and naproxen.

9. The method of any one of claims 1–3, wherein a dose of said prophylactic drug is administered from 30 minutes to 24 hours prior to the procedure of injecting a fluorocarbon emulsion into a patient.

10. The method of claim 9, wherein said prophylactic drug is administered in two or more doses.

11. The method of claim 9, comprising the further step of administering said prophylactic drug, either continuously or at intervals of time during the injection of a fluorocarbon emulsion into a patient.

12. A fluorocarbon emulsion comprising an effective amount of a TAPR-preventing or TAPR-opposing drug selected from the group consisting of steroidal and nonsteroidal anti-inflammatory agents, anti-pyretic agents, and non-narcotic analgesic agents.

13. The fluorocarbon emulsion of claim 12, wherein the TAPR-preventing or TAPR-opposing drug is indomethacin, ibuprofen, aspirin, naproxen, or combinations thereof.

14. The fluorocarbon emulsion of claim 12, wherein the TAPR-preventing or TAPR-opposing drug is a corticosteroid.

15. The fluorocarbon emulsion of claim 12, wherein the TAPR-preventing or TAPR-opposing drug is dexamethasone or methylprednisone.

16. An improvement in a method for parenteral administration of a fluorocarbon emulsion to a mammal in need thereof, wherein the improvement comprises administration of an effective amount of a TAPR-preventing or TAPR-opposing anti-inflammatory drug, wherein the anti-inflammatory drug is administered to the mammal before and concurrently with administration of the fluorocarbon emulsion.

17. The method of any one of claims 1–3 wherein said fluorocarbon emulsion comprises a fluorocarbon selected from the group consisting of brominated fluorocarbons, iodinated fluorocarbons and hydrogenated fluorocarbons.

18. The method of claim 17, wherein said fluorocarbon is a brominated fluorocarbon and said brominated fluorocarbon is perfluorooctylbromide.

19. The method of claim 18 wherein said drug is selected from the group consisting of steroidal anti-inflammatory agents, nonsteroidal anti-inflammatory agents, anti-pyretic agents, non-narcotic analgesic agents and combinations thereof.

20. The fluorocarbon emulsion of claim 12 wherein said fluorocarbon Emulsion comprises a fluorocarbon selected from the group consisting of brominated fluorocarbons, iodinated fluorocarbons and hydrogenated fluorocarbons.

21. The fluorocarbon emulsion of claim 20 wherein said fluorocarbon is a brominated fluorocarbon and said brominated fluorocarbon is perfluorooctylbromide.

22. The fluorocarbon emulsion of claim 21 wherein said drug is selected from the group consisting of steroidal anti-inflammatory agents, nonsteroidal anti-inflammatory agents, anti-pyretic agents, non-narcotic analgesic agents and combinations thereof.

23. The method of claim 16 wherein said fluorocarbon emulsion comprises a fluorocarbon selected from the group consisting of brominated fluorocarbons, iodinated fluorocarbons and hydrogenated fluorocarbons.

24. The method of claim 23 wherein said fluorocarbon is a brominated fluorocarbon and said brominated fluorocarbon is perfluorooctylbromide.

25. The method of claim 24 wherein said drug is selected from the group consisting of steroidal anti-inflammatory agents, nonsteroidal anti-inflammatory agents, anti-pyretic agents, non-narcotic analgesic agents and combinations thereof.

* * * * *